US012765814B2

(12) United States Patent
Chung et al.

(10) Patent No.: US 12,765,814 B2
(45) Date of Patent: Oct. 20, 2026

(54) INVASIVE MULTI-ELECTRODE ELECTROCHEMICAL SENSOR

(71) Applicant: UltraE Co. Ltd., Taichung City (TW)

(72) Inventors: Hsieh-Hsun Chung, Taichung City (TW); Jen-Lin Chang, Taichung City (TW)

(73) Assignee: UltraE Co. Ltd., Taichung City (TW)

( * ) Notice: Subject to any disclaimer, the term of this patent is extended or adjusted under 35 U.S.C. 154(b) by 205 days.

(21) Appl. No.: 18/639,188

(22) Filed: Apr. 18, 2024

(65) Prior Publication Data

US 2025/0261883 A1 Aug. 21, 2025

(30) Foreign Application Priority Data

Feb. 15, 2024 (TW) ................................ 113105391

(51) Int. Cl.

| | |
|---|---|
| ***A61B 5/1473*** | (2006.01) |
| ***A61B 5/145*** | (2006.01) |
| ***A61B 5/1486*** | (2006.01) |
| ***G01N 27/30*** | (2006.01) |

(52) U.S. Cl.

CPC ........ *A61B 5/1473* (2013.01); *A61B 5/14532* (2013.01); *A61B 5/14546* (2013.01);

(Continued)

(58) Field of Classification Search

CPC .............. A61B 5/1473; A61B 5/14532; A61B 5/14546; A61B 5/14865;

(Continued)

(56) References Cited

U.S. PATENT DOCUMENTS

| | | | |
|---|---|---|---|
| 2007/0060812 A1 | 3/2007 | Harel et al. |
| 2009/0178459 A1 | 7/2009 | Li et al. |

(Continued)

FOREIGN PATENT DOCUMENTS

| | | |
|---|---|---|
| CN | 113945622 A | 1/2022 |
| JP | 2011511665 A | 4/2011 |

(Continued)

OTHER PUBLICATIONS

Search Report appended to an Office Action, which was issued to Taiwanese counterpart application No. 112145898 by the TIPO on Feb. 17, 2025, with an English translation thereof.

(Continued)

*Primary Examiner* — Justin Xu

(74) *Attorney, Agent, or Firm* — MUNCY, GEISSLER, OLDS & LOWE, P.C.

(57) ABSTRACT

An invasive multi-electrode electrochemical sensor includes a substrate, plural wire electrodes and an axle. Each wire electrode includes an electrically conductive core and an insulating sheath that substantially covers, but exposes a proximal end and a distal end of, the electrically conductive core. Each wire electrode has a substrate section provided on the substrate and an invasion section extending outward from an edge of the substrate. The proximal end and distal end of the electrically conductive core of each wire electrode are located at the substrate section and invasion section of the wire electrode respectively. The invasion sections are wound around the axle spirally. The axle has a terminal end protruding beyond the distal ends of the invasion sections.

9 Claims, 14 Drawing Sheets

(52) U.S. Cl.
CPC ....... *A61B 5/14865* (2013.01); *G01N 27/308* (2013.01); *A61B 2562/0215* (2017.08); *A61B 2562/028* (2013.01); *A61B 2562/043* (2013.01); *A61B 2562/16* (2013.01); *A61B 2562/182* (2013.01); *A61B 2562/227* (2013.01)

(58) Field of Classification Search
CPC ...... A61B 2562/0215; A61B 2562/028; A61B 2562/043; A61B 2562/16; A61B 2562/182; A61B 2562/227; G01N 27/308
See application file for complete search history.

(56) References Cited

U.S. PATENT DOCUMENTS

| | | | | |
|---|---|---|---|---|
| 2011/0230735 | A1 | 9/2011 | Wolfe et al. | |
| 2011/0282172 | A1 | 11/2011 | Sass | |
| 2012/0323098 | A1 | 12/2012 | Moein et al. | |
| 2017/0360341 | A1* | 12/2017 | Brister | A61B 5/1495 |
| 2023/0277762 | A1* | 9/2023 | Duhamel | A61M 5/14248 604/66 |
| 2023/0293060 | A1* | 9/2023 | Duvall | A61B 5/1486 600/347 |

FOREIGN PATENT DOCUMENTS

| | | | |
|---|---|---|---|
| KR | 20210116007 | A | 9/2021 |
| KR | 20230049896 | A | 4/2023 |
| KR | 20230075445 | A | 5/2023 |
| TW | 201801359 | A | 1/2018 |
| TW | I862330 | B | 11/2024 |

OTHER PUBLICATIONS

Search Report appended to an Office Action, which was issued to Taiwanese counterpart application No. 113105389 by the TIPO on Nov. 1, 2024, with an English translation thereof.
Search Report appended to an Office Action, which was issued to Taiwanese counterpart application No. 113105391 by the TIPO on Jan. 3, 2025, with an English translation thereof.
An Office Action, which was issued to counterpart U.S. Appl. No. 18/641,951 by the USPTO on Feb. 23, 2026.
An Office Action, which was issued to counterpart U.S. Appl. No. 18/642,089 by the USPTO on Feb. 27, 2026.

* cited by examiner

INVASIVE MULTI-ELECTRODE ELECTROCHEMICAL SENSOR

BACKGROUND OF THE INVENTION

1. Technical Field

The present invention relates to an invasive electrochemical sensor.

2. Description of Related Art

Existing electrochemical sensors can be used in fluid detection and in that case are typically structured as test strips. An electrochemical test strip generally has a detection area to which a to-be-tested solution can be transferred in the form of a liquid drop or that can be immersed in the to-be-tested solution. However, existing electrochemical test strips cannot be used to perform invasive detection. When it comes to the continuous monitoring of biological/physiological parameters, an invasive detector is often more suitable than an existing non-invasive electrochemical test strip.

Therefore, it is an issue worth consideration by those working in the field to which the present invention pertains to provide an invasive electrochemical sensor that also has a relatively low production cost.

BRIEF SUMMARY OF THE INVENTION

The primary objective of the present invention is to provide a relatively low-cost invasive electrochemical sensor.

To achieve the above and other objectives, the present invention provides an invasive multi-electrode electrochemical sensor (hereinafter also referred to as the electrochemical sensor for short) that includes a substrate, a plurality of wire electrodes and an axle. Each wire electrode includes an electrically conductive core and an insulating sheath. Each insulating sheath substantially covers the corresponding electrically conductive core while leaving a proximal end and a distal end of the corresponding electrically conductive core exposed. Each wire electrode has a substrate section and an invasion section. The proximal end and the distal end of the electrically conductive core of each wire electrode are located at the substrate section and the invasion section of the wire electrode respectively. The substrate section of each wire electrode is located on the substrate. The invasion section of each wire electrode extends outward from an edge of the substrate, and the invasion sections of the wire electrodes are wound around the axle spirally. The axle has a terminal end protruding beyond the distal ends of the invasion sections.

The present invention is so designed that the mechanical strength of the invasion sections are enhanced by the axle. The invasion sections can be inserted into a detection target more easily, thereby increasing the application scenarios of the electrochemical sensor of the present invention.

DETAILED DESCRIPTION OF THE INVENTION

Please refer to FIG. 1 to FIG. 4 for the first embodiment of the present invention. The electrochemical sensor of the invention can be used to perform invasive detection on a host, and the host may be a human, an animal, or a plant. The electrochemical sensor can detect whether the host's body contains a target analyte, the concentration of the target analyte, and/or other to-be-detected values. The target analyte may be, for example but not limited to, glycated hemoglobin, blood sugar, a heavy metal, a nitrate, a nitrite, an allergen, formaldehyde, dissolved oxygen, uric acid, dopamine, ascorbic acid, potassium ferricyanide, acetaminophen, a halogen ion, a sulfur ion, an aqueous hydrogen peroxide solution, an arsenic (III) ion, a lead ion, a zinc ion, a chromium ion, phenols, an amino acid, or another similar compound. The to-be-detected value may be a physical parameter such as, but not limited to, a pH value or conductivity. The electrochemical sensor of the invention may also be implemented in such a way that it can be used in a non-invasive detection environment, e.g., to test a water sample taken from the environment or other aqueous solutions. In this embodiment, the electrochemical sensor includes a substrate 10, three wire electrodes 20, three gold fingers 30, and a cover plate 40.

The material of the substrate 10 may be, but is not limited to, polypropylene, polyethylene terephthalate; polyimide, polyethylene, polyurethane, or polycarbonate.

Figure 5:
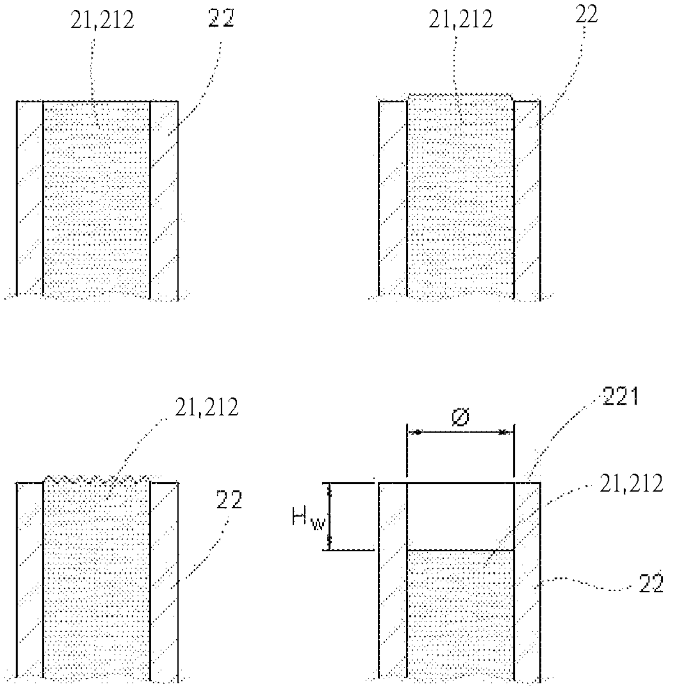
FIG. 5 shows sectional views of the distal ends of four electrically conductive cores.

Each wire electrode 20 includes an electrically conductive core 21 and an insulating sheath 22 (see FIG. 5). Each insulating sheath 22 substantially covers the corresponding electrically conductive core 21 while exposing a proximal end 211 and a distal end 212, or free end, of the corresponding electrically conductive core 21. In addition, each wire electrode 20 has a substrate section 23 and an invasion section 24. The proximal end 211 and the distal end 212 of the electrically conductive core 21 of each wire electrode 20 are located at the substrate section 23 and the invasion section 24 of the wire electrode 20 respectively. The substrate section 23 of each wire electrode 20 is provided on the substrate 10. The invasion section 24 of each wire electrode 20 extends outward from an edge of the substrate 10, and the length for which each invasion section 24 extends outward from the edge may be greater than 10 mm. In this embodiment, the invasion sections 24 of the three wire electrodes 20 are wound around one another in a spiral manner. Winding the invasion sections 24 together in a spiral manner is advantageous in that the accuracy of detection is enhanced by the short distance and low electrical resistance among the electrodes. The electrically conductive core 21 in the invasion section 24 of at least one of the wire electrodes 20 is different in material from the electrically conductive cores 21 of the other wire electrodes 20. In this embodiment, for example, the electrically conductive cores of the three wire electrodes serve separately as a working electrode, an auxiliary electrode, and a pseudo electrode/reference electrode. Depending on the analyte to be detected, the electrically conductive cores of the three wire electrodes may by, but are not limited to, the materials listed in Table 1. The insulating sheaths 22, on the other hand, are made of an insulating material to prevent the electrically conductive cores of different wire electrodes from direct electrical connection with one another and hence from forming a short circuit.

TABLE 1

| Working electrode | Auxiliary electrode | Pseudo electrode/ reference electrode | Analyte |
|---|---|---|---|
| Carbon | Carbon | Silver | Uric acid, dopamine, ascorbic acid, potassium ferricyanide, acetaminophen |
| Carbon | Platinum | Silver | Uric acid, dopamine, ascorbic acid, potassium ferricyanide, acetaminophen |
| Silver | Carbon | Silver chloride | Halogen ions |
| Nickle | Platinum | Carbon | Sulfur ion |
| Platinum | Platinum | Silver chloride | Aqueous hydrogen peroxide solution |
| Platinum | Gold | Silver chloride | Dissolved oxygen |
| Gold | Gold | Silver | Arsenic(III) ion, lead ion, zinc ion, chromium ion |
| Copper | Carbon | Silver | Phenols, amino acids |
| Bismuth | Carbon | Silver | Arsenic(III) ion, lead ion, zinc ion, chromium ion |

The wire electrodes can be viewed as metallic wire ultramicroelectrodes (MWUME) when the diameter Ø of each electrically conductive core 21 is less than or equal to 25 μm, as metallic wire microelectrodes (MWME) when the diameter Ø of each electrically conductive core 21 is greater than 25 μm and less than 1000 μm, or as metallic wire electrodes (MWE) when the diameter Ø of each electrically conductive core 21 is greater than or equal to 1000 μm.

The gold fingers 30 are provided on the substrate 10. The electrically conductive core 21 in the substrate section 23 of each wire electrode 20 (e.g., the proximal end 211 of each electrically conductive core 21) is electrically connected to the corresponding gold finger 30. The electrical connection between each electrically conductive core 21 and the corresponding gold finger 30 may be formed by, for example but not limited to, soldering or application of electrically conductive tape. The gold fingers 30 may be printed on the substrate 10 by screen printing for example, and the material of the gold fingers 30 may be printed carbon paste or printed silver paste for example. The printed carbon paste or printed silver paste may further receive a surface treatment by, for example, being sputter-coated with a metal such as platinum, gold, copper, or silver. In this embodiment, the gold fingers 30 extend to an edge of the substrate 10.

The cover plate 40 is provided on the substrate 10 such that the entire substrate sections 23 of the wire electrodes 20 are fixed between the cover plate 40 and the substrate 10.

Figure 6:
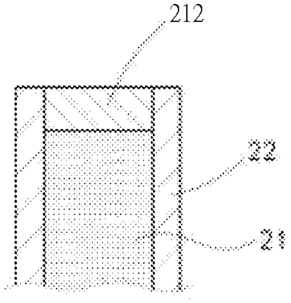
FIG. 6 shows a sectional view of the distal end of an electrically conductive core in another embodiment.

Referring to FIG. 5, the distal end of each electrically conductive core 21 may receive a surface treatment so as to have the configuration of being flush with the corresponding end face of the corresponding insulating sheath 22, or protruding from the corresponding end face of the corresponding insulating sheath 22, or having an irregular surface, or being sunken into the corresponding end face of the corresponding insulating sheath 22. One way of implementing the wire electrodes is to make the distal end 212 of each electrically conductive core 21 sunken into an end face 221 of the corresponding insulating sheath 22 while satisfying the relationship $H_w/Ø<50$, where $H_w$ is the depth to which the distal end 212 is sunken into the end face 221. This sunken configuration leaves room for subsequent chemical modification of the distal ends of the electrically conductive cores. For example, the recess formed at the aforesaid end face of each insulating sheath may be filled with an enzyme layer (not shown). Besides, referring to FIG. 6, the distal end 212 of at least one of the electrically conductive cores 21 is made of a material different from the material of the other portion of the electrically conductive core 21. For example, the distal end of this at least one electrically conductive core is made of carbon while the other portion of the electrically conductive core is made of copper in order to adapt to different detection environments.

Figure 7:
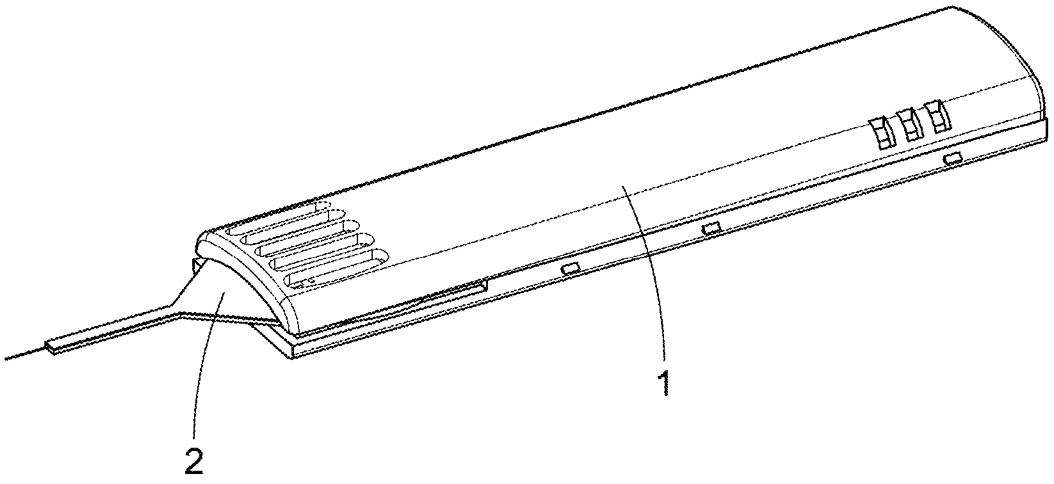
FIG. 7 shows the electrochemical sensor of the present invention used in combination with an electrochemical sensing relay.

Referring to FIG. 7, the electrochemical sensor according to the embodiment shown in FIG. 1 to FIG. 4 can be used in combination with an electrochemical sensing relay 1. The electrochemical sensing relay 1 is configured to be electrically connected to each and every gold finger of the electrochemical sensor 2 and to relay the signals sensed by the electrochemical sensor to a remote receiving unit (e.g., a smartphone, a computer, or a cloud server) in order to perform further computation and/or display the computation result.

Figure 8:
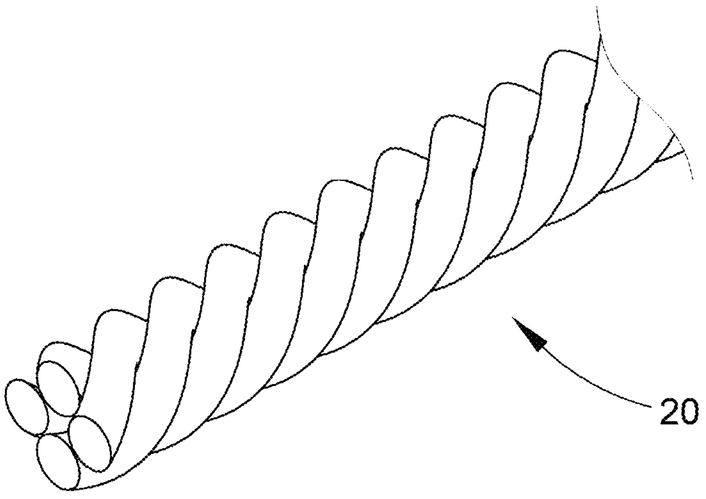
FIG. 8 shows a way of implementing the invasion sections of the wire electrodes in the present invention.
Figure 9:
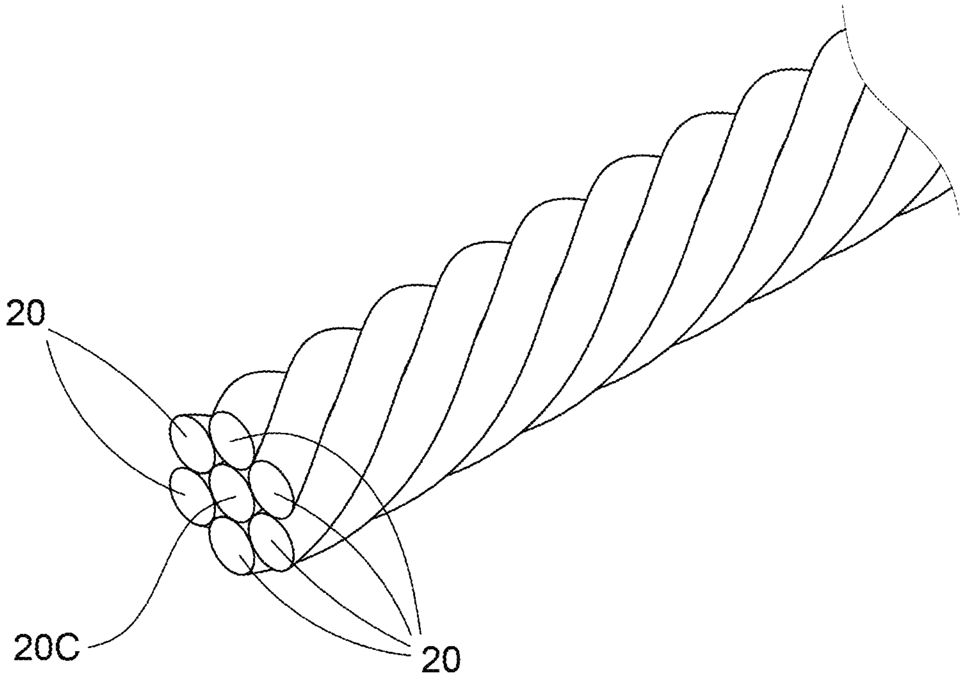
FIG. 9 shows another way of implementing the invasion sections of the wire electrodes in the present invention.

It should be pointed out that the number of the wire electrodes can be adjusted. For example, in the embodiment shown in FIG. 8, the spirally wound invasion sections of the four wire electrodes 20 can be used to detect more analytes at the same time than when fewer wire electrodes are provided, and as shown in FIG. 9, the invasion sections of six wire electrodes may be spirally wound around the invasion section of a central wire electrode 20*c* that extends along a straight line, i.e., with the invasion section of at least one wire electrode that extends along a straight line serving as an axis around which the invasion sections of the other wire electrodes are spirally wound.

Figure 1:
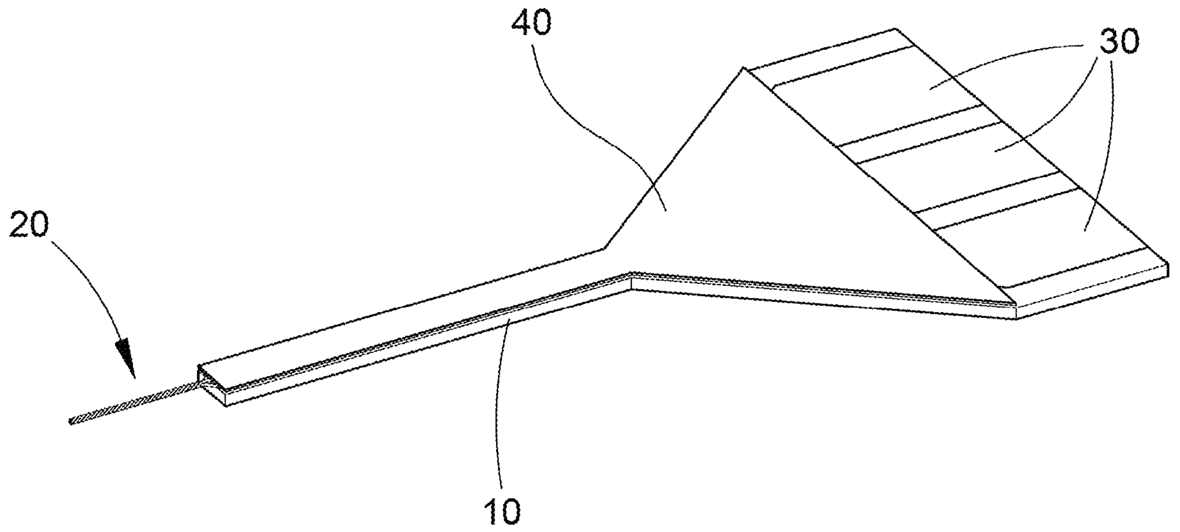
FIG. 1 is a perspective view of the first embodiment of the present invention.
Figure 2:
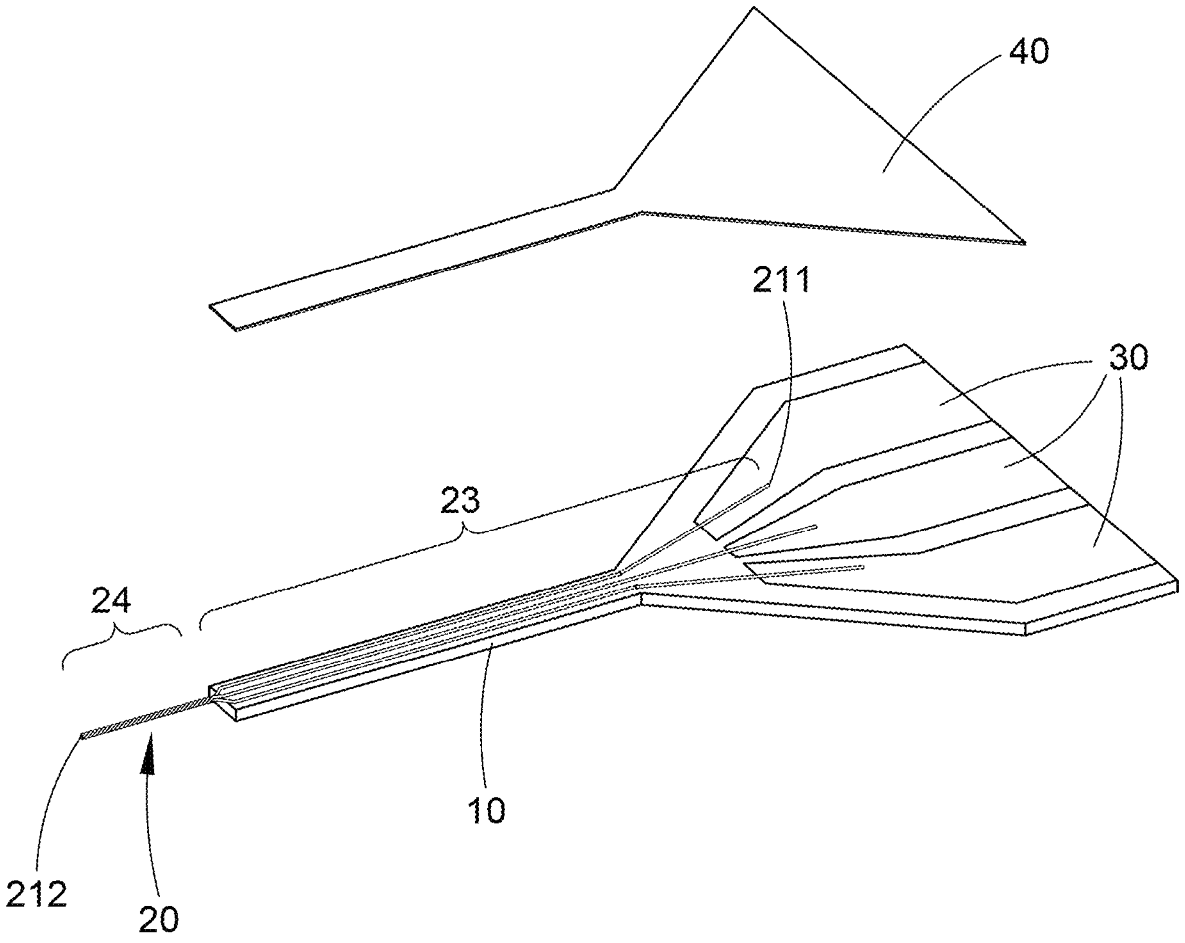
FIG. 2 is an exploded view of the first embodiment of the present invention.
Figure 3:
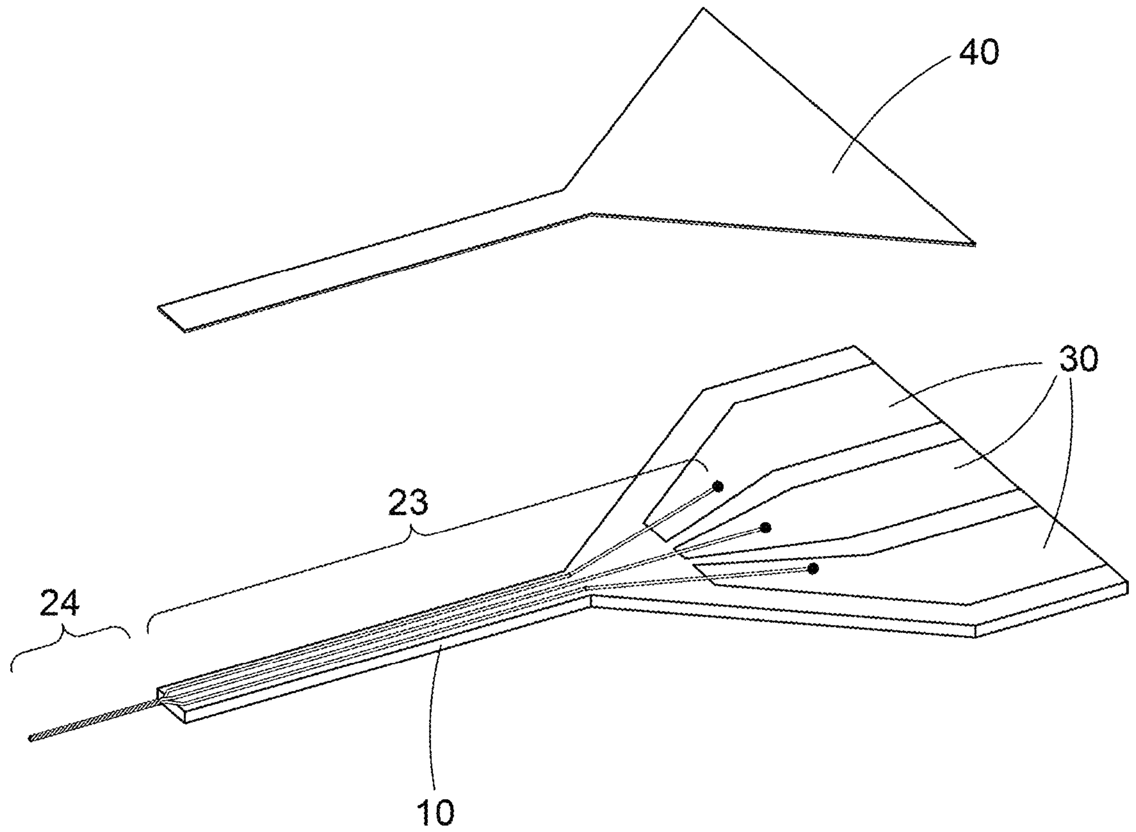
FIG. 3 is another exploded view of the first embodiment of the present invention, showing in particular how each electrically conductive core is electrically connected to the corresponding gold finger by soldering.
Figure 4:
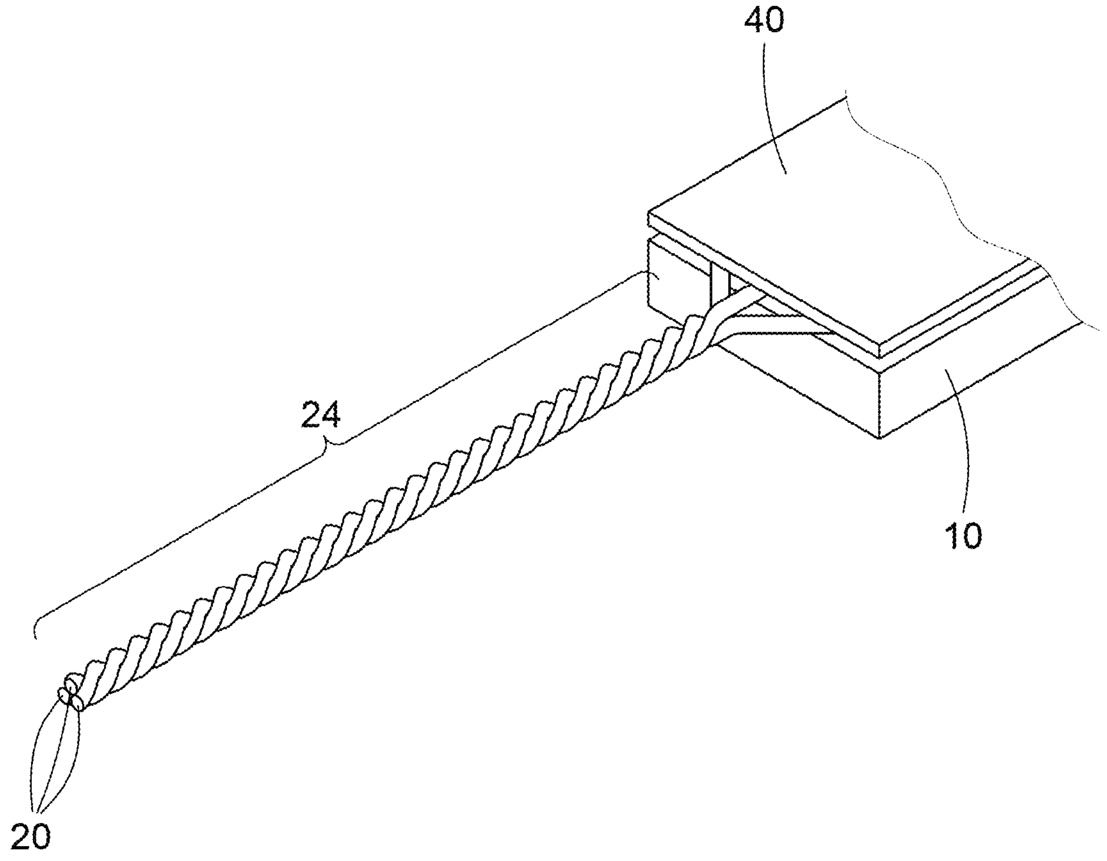
FIG. 4 is a partial enlarged view of the first embodiment of the present invention.
Figure 10:
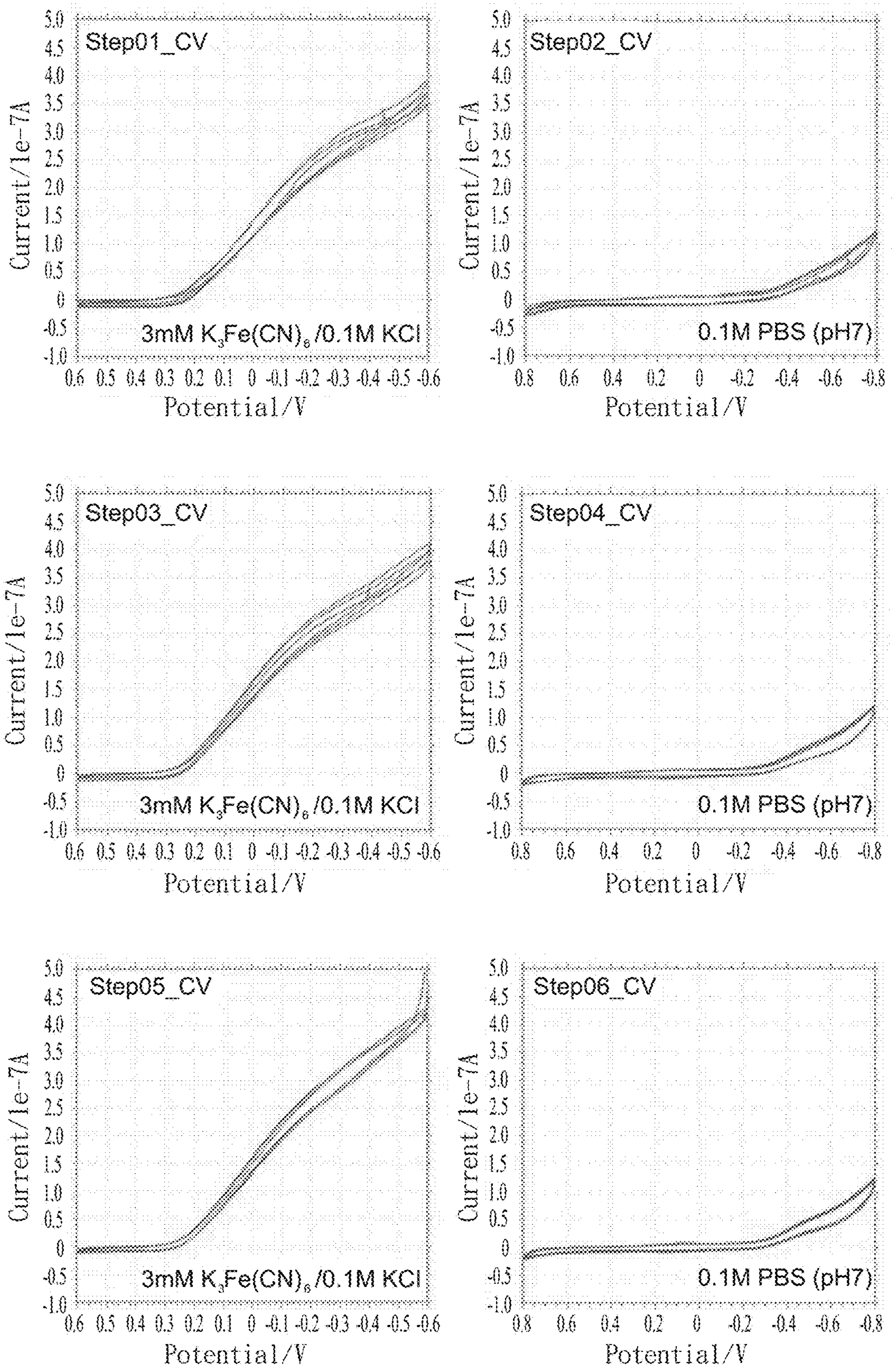
FIG. 10 shows the reproducibility test results of the electrochemical sensor of the present invention.

Referring to FIG. 10, a reproducibility test was conducted in which a plurality of electrochemical sensors as shown in FIG. 1 took turns being immersed in each of two different aqueous solutions for three times. The test results show that the detection result of each aqueous solution was highly reproducible with the electrochemical sensor of the present invention.

Figure 11:
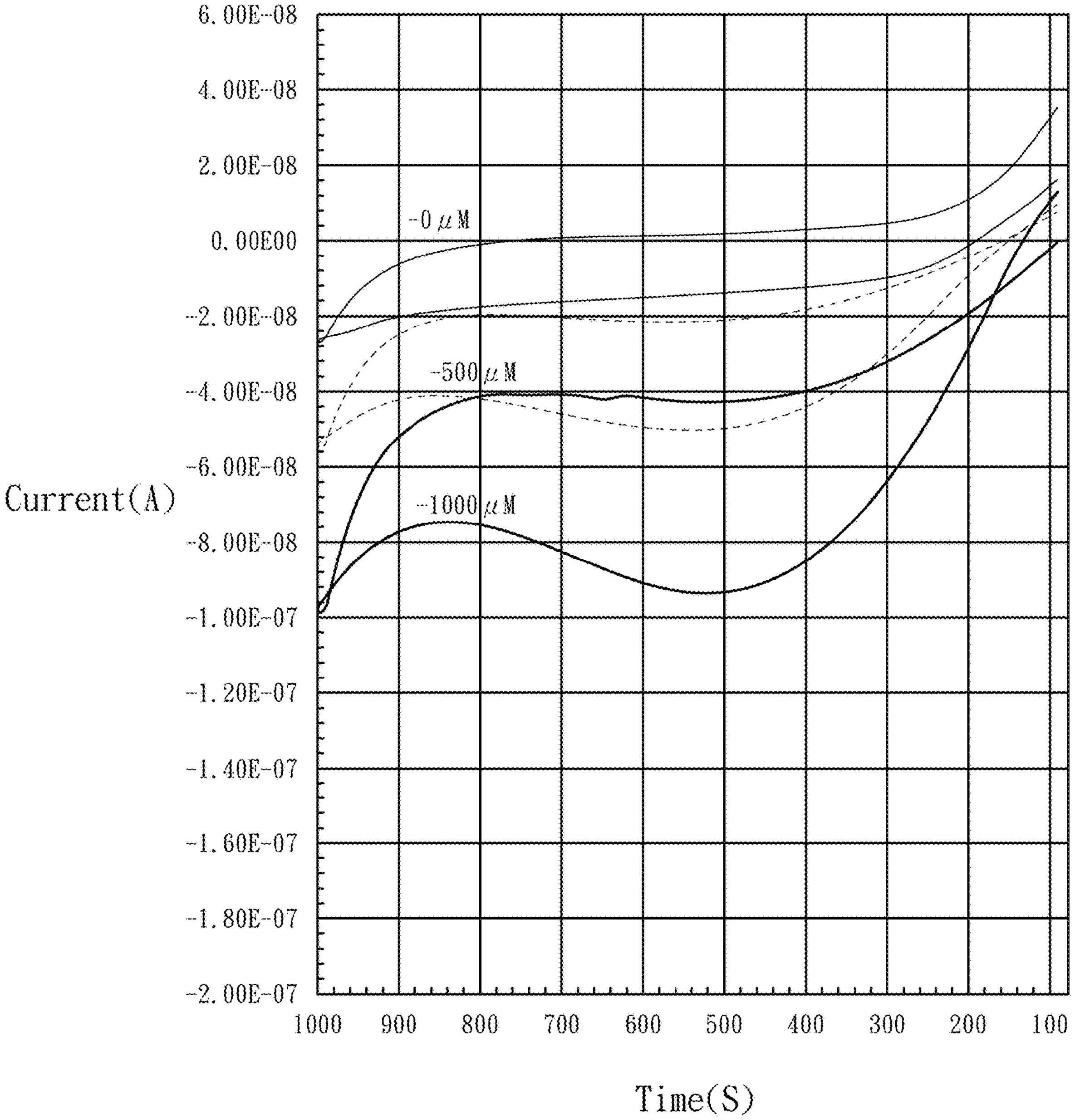
FIG. 11 shows cyclic voltammogram traces obtained by immersing the electrochemical sensor of the present invention in aqueous hydrogen peroxide solutions of different concentrations.

Referring to FIG. 11, an electrochemical sensor with three wire electrodes was immersed in 0.1 M PBS (phosphate-buffered saline), 500 μM aqueous hydrogen peroxide ($H_2O_2$) solution, and 1000 μM aqueous hydrogen peroxide solution separately. The material of the major portions of the electrically conductive cores of the wire electrodes was carbon while the material of the distal ends of the electrically conductive cores was platinum. The test results show that the electrochemical sensor of the present invention was indeed capable of detecting different oxidation and reduction potentials in aqueous hydrogen peroxide solutions of different concentrations.

Figure 12:
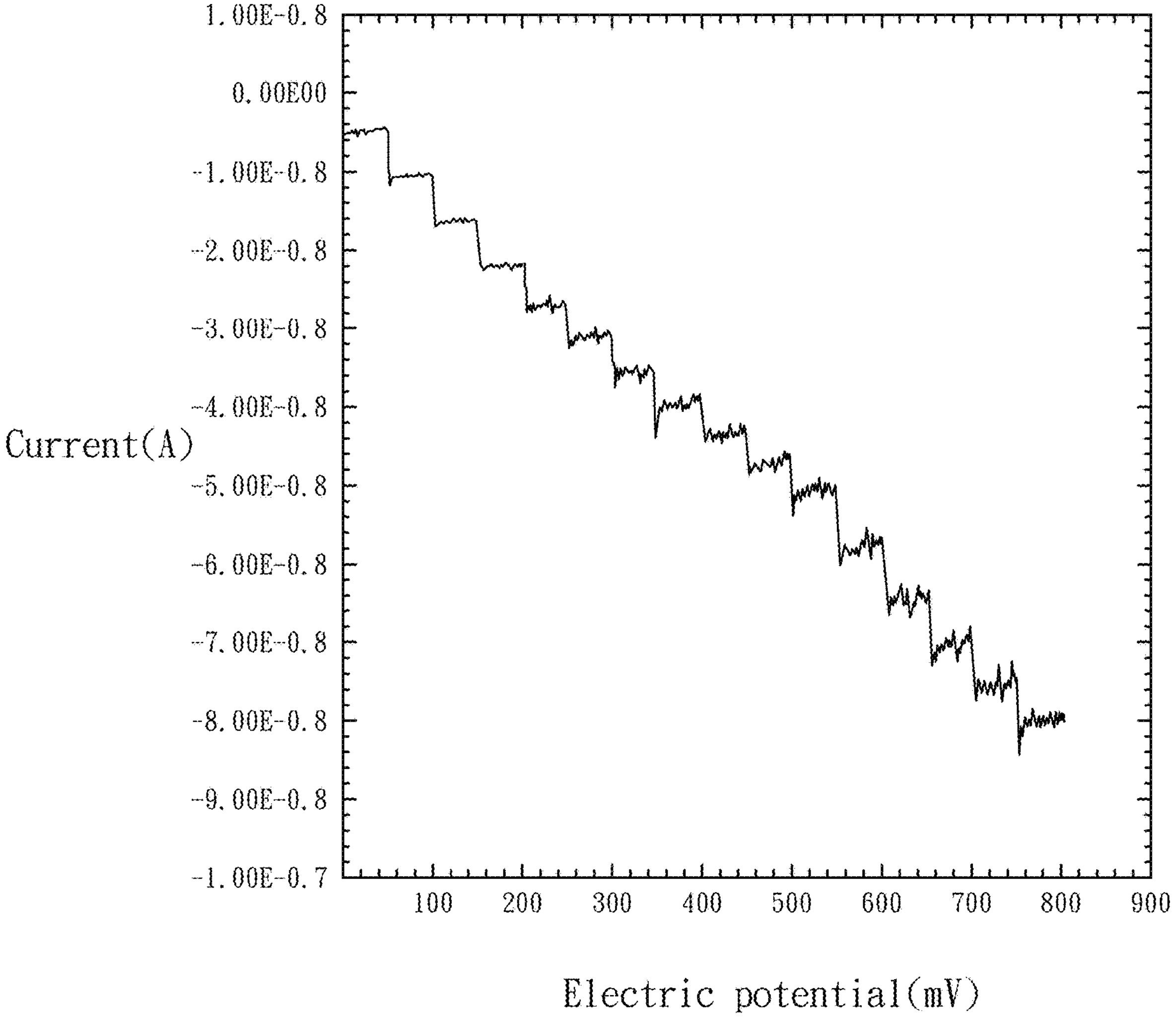
FIG. 12 shows a current-time graph obtained by detecting an aqueous hydrogen peroxide solution with the electrochemical sensor of the present invention by amperometry.
Figure 13:
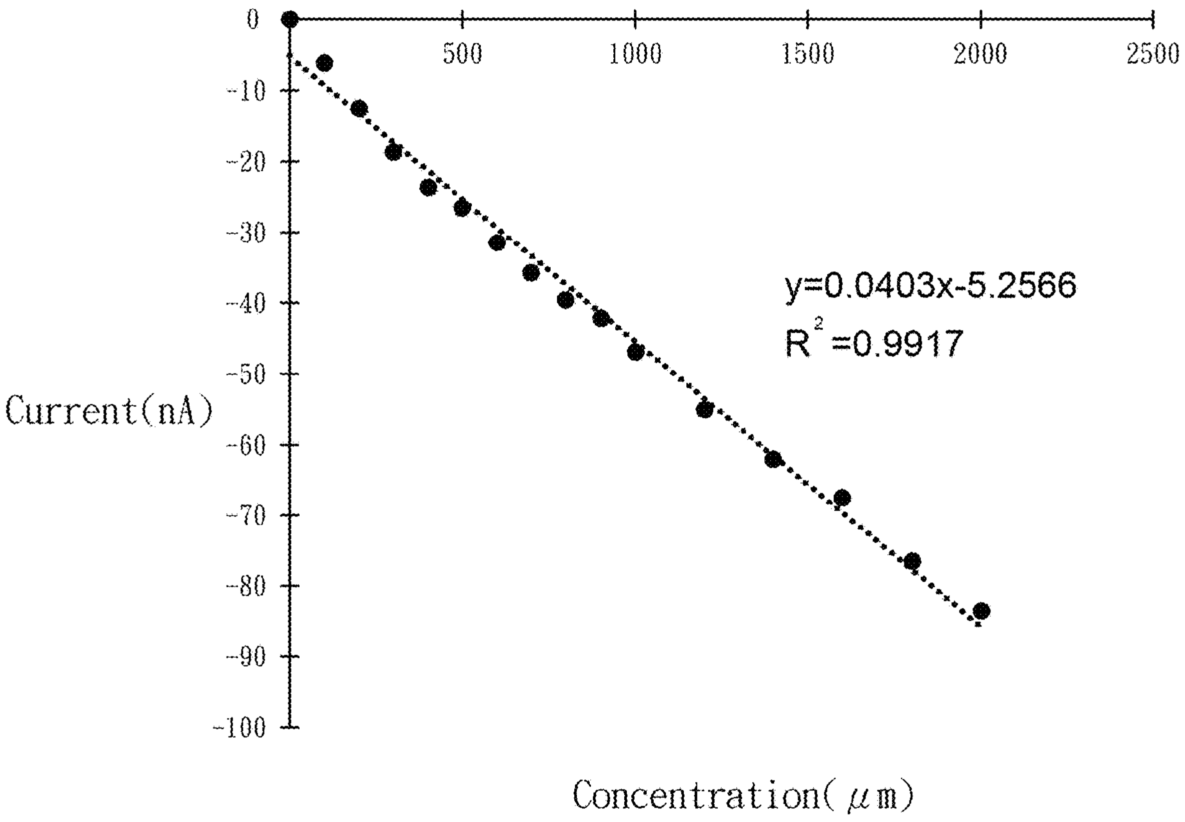
FIG. 13 shows a linear regression line fitted to the data points on a current-concentration graph obtained by detecting an aqueous hydrogen peroxide solution with the electrochemical sensor of the present invention by amperometry.

Referring to FIG. 12, the applicant used amperometry to test the performance of the electrochemical sensor of the present invention in detecting aqueous hydrogen peroxide solutions. The electrochemical sensor used in the test had three wire electrodes, with the material of the major portions of the electrically conductive cores of the wire electrodes being carbon, and the material of the distal ends of the electrically conductive cores being platinum. The applicant used amperometry together with the working parameters in Table 2 to detect aqueous hydrogen peroxide solutions of different concentrations. More specifically, the concentration of an aqueous hydrogen peroxide solution was adjusted every 50 seconds. Each of the first ten adjustments involved increasing the concentration by 100 μM, and each of the last five adjustments involved increasing the concentration by 200 μM. The final concentration was 2000 μM. The oxidation voltage was fixed at 600 mV. The test results show that the electrochemical sensor of the invention was able to detect the changes in concentration of the aqueous hydrogen peroxide solution sensitively, and that the detected current values are highly linearly correlated to the changes in concentration (see FIG. 13), indicating that the electrochemical sensor of the invention has high accuracy.

TABLE 2

| Elapsed time (s) | Concentration of aqueous hydrogen peroxide solution (μM) |
|---|---|
| 0 | 0 |
| 50 | 100 |
| 100 | 200 |
| 150 | 300 |
| 200 | 400 |
| 250 | 500 |
| 300 | 600 |
| 350 | 700 |
| 400 | 800 |
| 450 | 900 |
| 500 | 1000 |
| 550 | 1200 |
| 600 | 1400 |
| 650 | 1600 |
| 700 | 1800 |
| 750 | 2000 |

Figure 14:
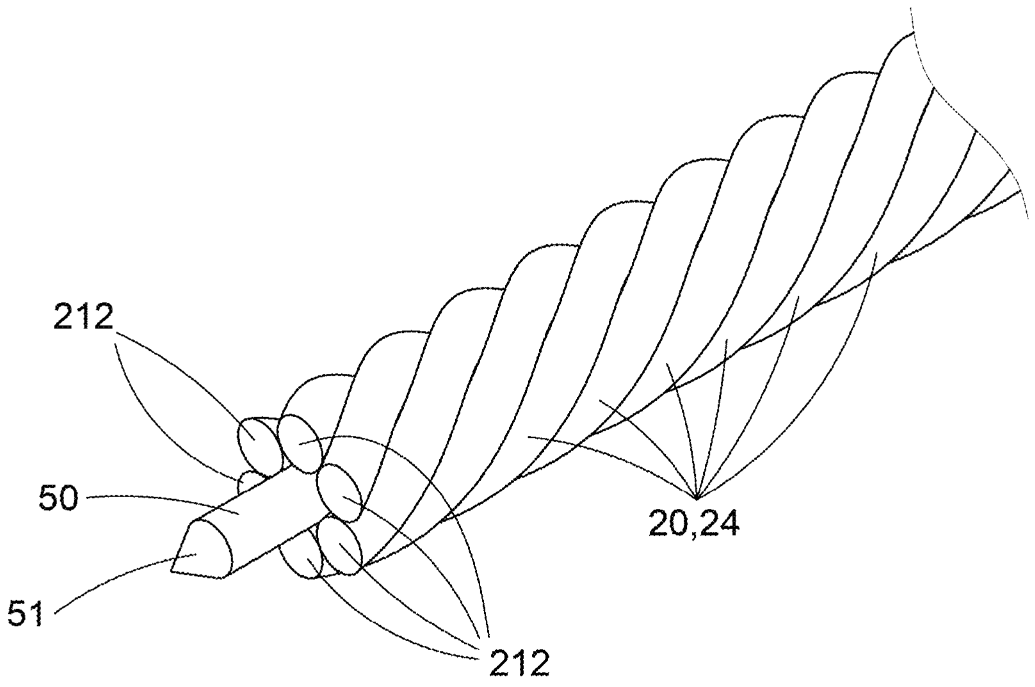
FIG. 14 shows still another way of implementing the invasion sections of the wire electrodes in the present invention.
Figure 15:
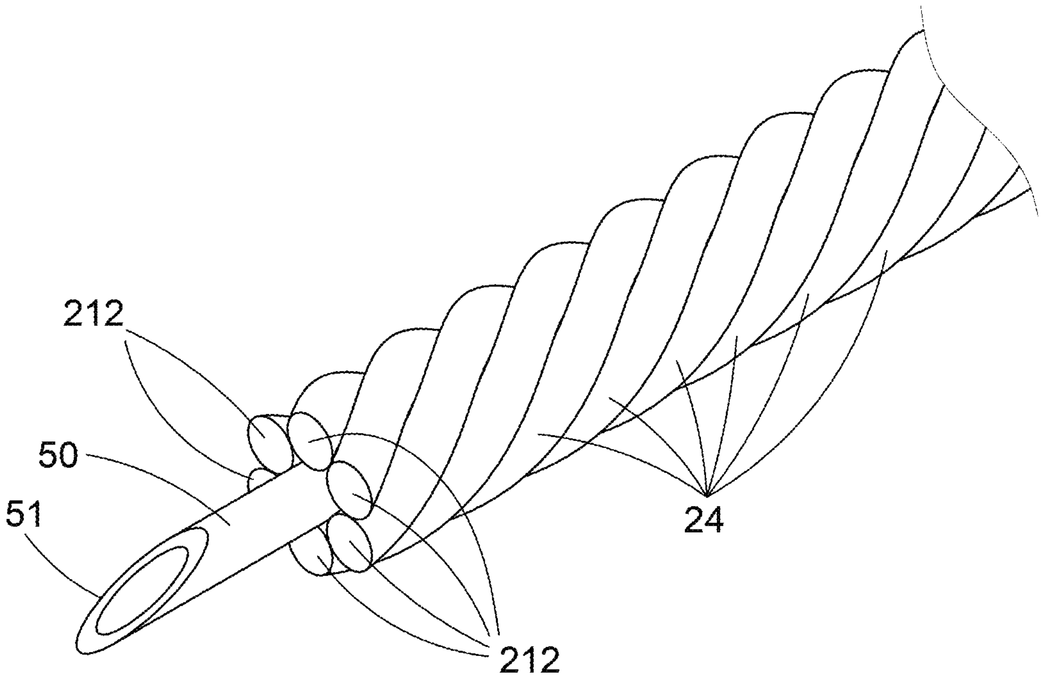
FIG. 15 shows yet another way of implementing the invasion sections of the wire electrodes in the present invention.

The embodiment shown in FIG. 14 is similar to the embodiment in FIG. 9, the major difference being that the electrochemical sensor in FIG. 14 includes an axle 50, and that the central wire electrode 20*c* in FIG. 9 is replaced by the axle 50 while the invasion sections 24 of the other wire electrodes 20 are wound around the axle 50 spirally. A portion of the axle is configured to be fixed to the substrate (not shown). The portion of the axle 50 around which the invasion sections 24 are spirally wound extends along a straight line. The axle 50 has a terminal end 51, and the terminal end 51 protrudes beyond the distal ends 212 of the invasion sections 24. In this embodiment, the terminal end 51 is solid and pointed and serves to change the structural strength of the invasion sections 24 so that the invasion sections 24 can be easily inserted into a detection target (e.g., soil or a plant) without the help of an additional placing device. The embodiment shown in FIG. 15 is similar to the embodiment in FIG. 14, the major difference being that the terminal end 51 of the axle 50 in FIG. 15 is hollow and pointed and serves also to change the structural strength of the invasion sections 24. The hollow terminal end 51 helps disturb the tissue into which it is inserted, so that the tissue can contact the distal ends 212 of the invasion sections 24 easily through capillary action for example, thereby facilitating detection. The axle 50 may be a non-metallic, non-conductor wire, whose material may be, for example, ceramic, silicon dioxide, plastic, acrylic, or a polymer such as polypropylene (PP), polycarbonate (PC), or polyethylene (PE).

Figure 16:
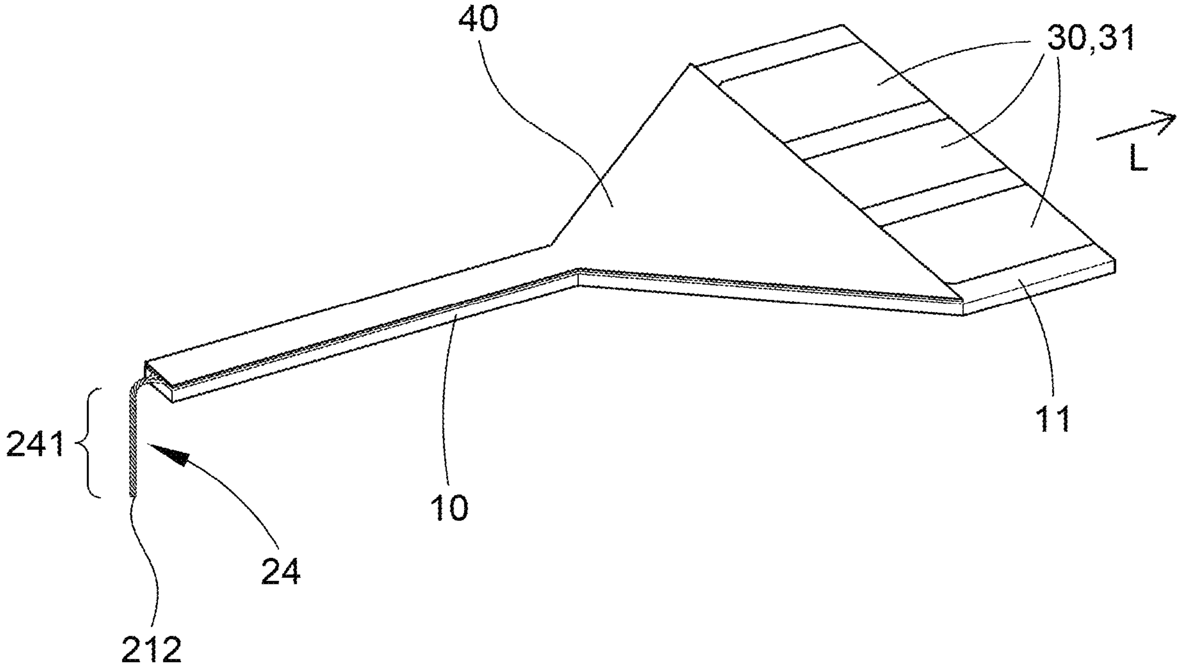
FIG. 16 shows another way of implementing the electrochemical sensor of the present invention.

Referring to FIG. 16, the embodiment shown therein is similar to the embodiment in FIG. 1. The portion of each gold finger 30 that is not covered by the cover plate 40 is defined as an exposed section 31. The exposed sections 31 are parallel to one another and extend in an insertion direction L. The gold fingers 30 are provided on a working surface 11 of the substrate 10. The invasion section 24 of each wire electrode has a front-side portion 241, and the distal end 212 of the electrically conductive core of each wire electrode is located at the front-side portion of the invasion section of the wire electrode. The front-side portions 241 extend in a direction that is not parallel to the insertion direction L or the working surface 11. In this embodiment, the front-side portions 241 are perpendicular to the working surface 11. Another possible way of implementing the electrochemical sensor is to provide the invasion sections 24 with flexibility so that a user can adjust the extending direction of the front-side portions 241 according to the geometric properties of the detection target.

What is claimed is:

1. An invasive multi-electrode electrochemical sensor, comprising:

a substrate;

a plurality of wire electrodes, wherein each of the plurality of wire electrodes comprises an electrically conductive core and an insulating sheath, the electrically conductive core has a proximal end, a distal end, and a main portion extending between the proximal end and the distal end, the insulating sheath covers the main portion of the electrically conductive core while exposing the proximal end and the distal end of the electrically conductive core such that the electrically conductive core of one of the plurality of wire electrodes is prevented from being in direct electrical connection with the electrically conductive core of each of other ones of the plurality of wire electrodes, the plurality of wire electrodes each has a substrate section and an invasion section, the substrate section includes the proximal end of the electrically conductive core, the invasion section includes the distal end of the electrically conductive core, the substrate section is provided on the substrate, and the invasion section extends outward from an edge of the substrate; and an axle, the invasion section of the one of the plurality of wire electrodes being wound together with the invasion section of each of the other ones of the plurality of wire electrodes around the axle spirally, the axle having a terminal end protruding beyond the distal end of the invasion section.

2. The invasive multi-electrode electrochemical sensor of claim 1, wherein the terminal end is pointed.

3. The invasive multi-electrode electrochemical sensor of claim 1, wherein the terminal end is solid.

4. The invasive multi-electrode electrochemical sensor of claim 1, wherein the terminal end is hollow.

5. The invasive multi-electrode electrochemical sensor of claim 1, further comprising a cover plate provided on the substrate such that the substrate section is at least partially fixed between the cover plate and the substrate.

6. The invasive multi-electrode electrochemical sensor of claim 1, wherein the invasion section extends outward from the edge with a length of greater than 10 mm.

7. The invasive multi-electrode electrochemical sensor of claim 1, wherein the main portion has a first part which is connected to the proximal end, and a second part which extends spirally between the first part and the distal end, the substrate section further includes the first part of the electrically conductive core, the invasion section further includes the second part of the electrically conductive core, and the second part is covered by the insulating sheath.

8. The invasive multi-electrode electrochemical sensor of claim 1, wherein the distal end of the electrically conductive core of the one of the plurality of wire electrodes is flush with the distal end of the electrically conductive core of each of the other ones of the plurality of wire electrodes.

9. The invasive multi-electrode electrochemical sensor of claim 1, wherein a portion of the axle is configured to be fixed to the substrate, and wherein the portion of the axle around which the invasion section is spirally wound extends along a straight line.

* * * * *